United States Patent [19]

Manicom

[11] Patent Number: 5,070,871
[45] Date of Patent: Dec. 10, 1991

[54] ANAESTHETIC VALVE FOR CONVERTING BETWEEN MAPLESON 'A' AND 'D' SYSTEMS

[76] Inventor: Anthony W. Manicom, 173 Blanford Road, Northriding, Randburg, Transvaal, South Africa

[21] Appl. No.: 458,454

[22] Filed: Dec. 28, 1989

[30] Foreign Application Priority Data

Dec. 28, 1988 [ZA] South Africa .................. 88/9674

[51] Int. Cl.⁵ ............................................. A62B 9/02
[52] U.S. Cl. ........................... 128/205.24; 128/204.18; 128/204.26
[58] Field of Search .............. 128/205.24, 204.18, 128/207.14, 911, 912, 204.26

[56] References Cited

U.S. PATENT DOCUMENTS

| | | | |
|---|---|---|---|
| 3,251,359 | 5/1966 | Ismach | 128/205.24 |
| 3,905,362 | 9/1975 | Eyrick et al. | 128/205.19 |
| 3,938,551 | 2/1976 | Henkin | 128/205.24 |
| 4,096,858 | 6/1978 | Eyrick et al. | 128/205.16 |
| 4,180,066 | 12/1979 | Milliken et al. | 128/205.24 |
| 4,245,633 | 1/1981 | Erceg | 128/205.24 |
| 4,249,528 | 2/1981 | Mathes | 128/205.24 |
| 4,281,652 | 8/1981 | Miller | 128/205.17 |
| 4,676,239 | 6/1987 | Humphrey | 128/205.17 |
| 4,694,825 | 9/1987 | Slemmer et al. | 128/205.24 |
| 4,702,240 | 10/1987 | Chaoui | 128/205.24 |
| 4,702,241 | 10/1987 | Gravenstein et al. | 128/205.19 |
| 4,791,922 | 12/1988 | Lindsay-Scott et al. | 128/205.28 |
| 4,846,167 | 7/1989 | Tibbals | 128/202.27 |

FOREIGN PATENT DOCUMENTS

| | | | |
|---|---|---|---|
| 78/4626 | 8/1979 | South Africa | 128/205.24 |
| 81/6160 | 8/1981 | South Africa | 128/205.24 |
| 581814 | 10/1946 | United Kingdom | 128/205.24 |
| 602890 | 6/1948 | United Kingdom | 128/205.24 |
| 873006 | 7/1961 | United Kingdom | 128/205.24 |
| 883032 | 11/1961 | United Kingdom | 128/205.24 |
| 1027633 | 4/1966 | United Kingdom | 128/205.24 |
| 1432171 | 4/1976 | United Kingdom | 128/205.24 |
| 1444607 | 8/1976 | United Kingdom | 128/205.24 |
| 1493387 | 11/1977 | United Kingdom | 128/205.24 |
| 2162070 | 1/1986 | United Kingdom | 128/205.24 |

OTHER PUBLICATIONS

*Anaesthesia*, 1983, vol. 38, pp. 361-372, Humphrey, "A New Anaesthetic Breathing System . . . ".
"The Johannesburg A-D Circuit Switch" published in The British Journal of Anaesthesia. (1979), 51, 1185.

*Primary Examiner*—Edgar S. Burr
*Assistant Examiner*—Kimberly L. Asher

[57] ABSTRACT

A valve for an anaesthetic rebreathing system includes a valve body and a valve closure member situated within the valve body. The valve can be converted between a Mapleson A and a Mapleson D configuration. The valve body includes a fresh gas inlet, a fresh gas outlet, a fresh gas conduit in communication with the fresh gas inlet and the fresh gas outlet, an expired gas inlet/outlet port, a waste gas outlet, an expired gas conduit in communication with the expired gas inlet/outlet port and the waste gas outlet, a reservoir bag inlet/outlet port and a reservoir bag conduit in communication with the reservoir bag inlet/outlet port. All the conduits converge at a node within which the valve closure member is operable to isolate the expired gas inlet/outlet port and the waste gas outlet from the reservoir bag inlet/outlet port in a first position thereof and to isolate the fresh gas inlet and the fresh gas outlet from the reservoir bag inlet/outlet port in a second position thereof.

9 Claims, 3 Drawing Sheets

ANAESTHETIC VALVE FOR CONVERTING BETWEEN MAPLESON 'A' AND 'D' SYSTEMS

BACKGROUND TO THE INVENTION

This invention relates to a valve for an anaesthetic rebreathing system and is a development on the valve described and claimed in RSA Patent No. 78/4626—Manicom, Schoonbee—which describes such a valve.

The terms "anaesthetic system" and "anaesthetic rebreathing system" are used, in this specification, to denote the connecting apparatus between the anaesthetic machine and the face mask or endotracheal tube which connects to a patient, except where the context indicates otherwise.

A simple anaesthetic breathing system comprises two lengths of flexible tubing of suitable dimensions which connect the patient's airway to an anaesthetic gas supply machine. The two lengths of flexible tubing constitute the inspiratory and the expiratory limbs of a breathing circuit and converge at the patient's airway so that fresh gas flows from the anaesthetic gas supply machine, through the inspiratory limb of the circuit, to the patient's airway. Exhaled gas flows out through the expiratory limb of the circuit and is vented at the end of the expiratory limb. In a simple anaesthetic breathing system therefore, the flow of gas remains unidirectional.

In anaesthetic rebreathing systems, unlike simple anaesthetic breathing systems, a compliant reservoir bag is placed in the circuit and this provides for intermittent reversal of gas flow in whichever of the inspiratory or expiratory limbs contains the reservoir bag. When the inspiratory limb contains the reservoir bag the system is classified as a Mapleson A system and when the expiratory limb contains the reservoir bag the system is classified as a Mapleson D system.

A Mapleson A system is desirable when a patient breathes spontaneously, without being aided by manipulation of the reservoir bag, and such a system allows a low level of fresh gas flow to be used which prevents the wastage of costly anaesthetic gases. A Mapleson D system is desirable when the breathing of a patient is mechanically or manually controlled, for example, by compression of the reservoir bag. The rebreathing of exhaled gases inter alia provides useful humidification in the patient's airway.

It is important that in a particular situation the mode of breathing, namely spontaneous breathing or controlled breathing, is appropriate. If the inappropriate mode of breathing is used, at least twice the fresh gas flow would be required to prevent retention of carbon dioxide produced by the patient. This would be wasteful.

SUMMARY OF THE INVENTION

According to the invention a valve for an anaesthetic rebreathing system includes a valve body and a valve closure member situated within the valve body, the valve body including a fresh gas inlet, a fresh gas outlet, a fresh gas conduit in communication with the fresh gas inlet and the fresh gas outlet, an expired gas inlet/outlet port, a waste gas outlet, an expired gas conduit in communication with the expired gas inlet/outlet port and the waste gas outlet, a reservoir bag inlet/outlet port and a reservoir bag conduit in communication with the reservoir bag inlet/outlet port, the conduits converging at a node within which the valve closure member is operable to isolate the expired gas inlet/outlet port and the waste gas outlet from the reservoir bag inlet/outlet port in a first position thereof and to isolate the fresh gas inlet and the fresh gas outlet from the reservoir bag inlet/outlet port in a second position thereof.

For additional safety, the valve closure member may be adapted for location in an intermediate position in which the fresh gas inlet, the fresh gas outlet, the expired gas inlet/outlet port and the waste gas port are all in communication with the reservoir bag inlet/outlet port. This can be done by forming the valve closure member as two relatively large cylindrical plugs, which are adapted to act as two independent valve closure members in a complemental, cylindrical slideway into which the conduits open, each at its own seat, the plugs being joined to each other by a reduced central neck region which is dimensioned to interconnect all the inlets, outlets and ports in the intermediate position. In the normal, operative positions of the valve closure member, the neck region thereof is dimensioned merely to interconnect the conduits converging at the node—to isolate the expired gas inlet/outlet port and the waste gas outlet from the reservoir bag inlet/outlet port in one position thereof and to isolate the fresh gas inlet and the fresh gas outlet from the reservoir bag inlet/outlet port in a second position thereof.

The waste gas outlet is adapted for connection to a scavenging system and may conveniently include a back pressure control for controlling back pressure in the expired gas conduit, the back pressure control being adjustable between a first setting, in which expired gas may flow freely out of the waste gas outlet, and one or more settings in which the waste gas outlet is at least partly occluded. In the first setting the back pressure in the expired gas conduit is maintained at a relatively low level and in the remaining settings the outflow of the expired gas is at least partially restricted to maintain the back pressure in the expiratory limb of the system at a predeterminable, higher level.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE DRAWINGS

The present invention will become more fully understood from the detailed description given hereinbelow and the accompanying drawings which are given by way of illustration only, and Thus are not limitative of the present invention, and wherein.

DESCRIPTION OF AN EMBODIMENT OF THE INVENTION

Figure 1:
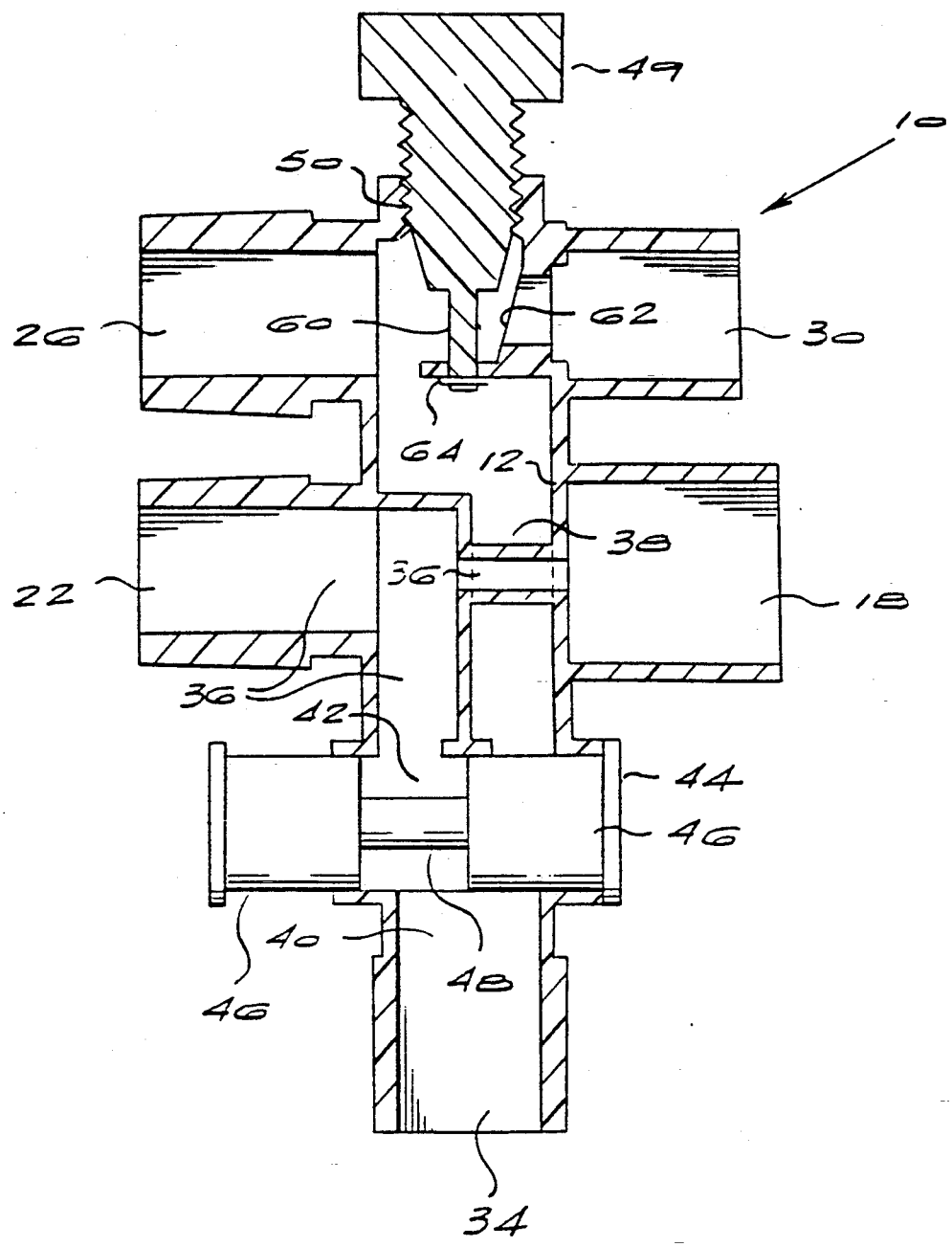
FIG. 1 is a section through the valve of the invention with the valve closure member thereof positioned to convert the valve to a "Mapleson A" configuration.
Figure 2:
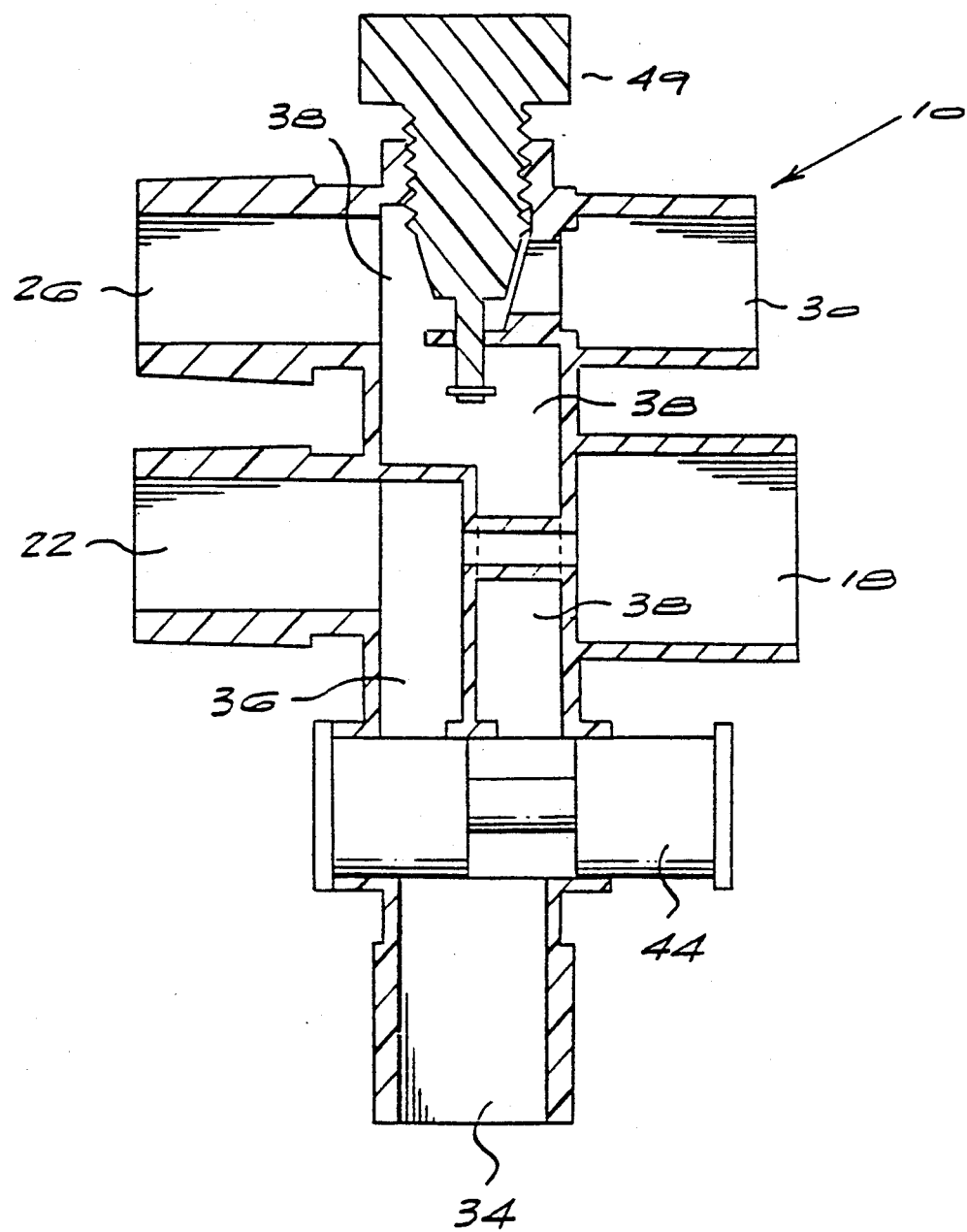
FIG. 2 is a similar section of the valve, with the valve closure member positioned to convert the valve to a "Mapleson D" configuration.
Figure 3:
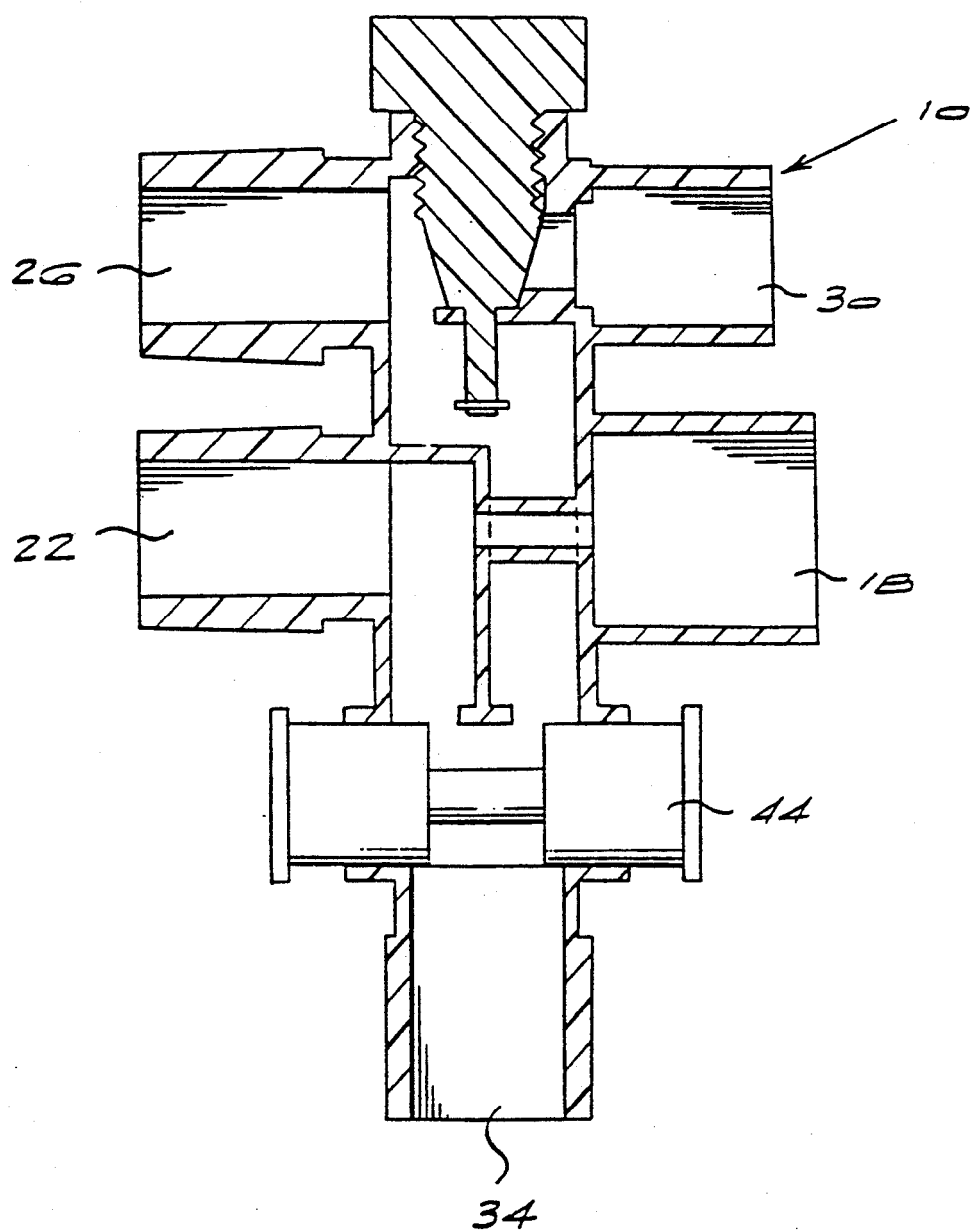
FIG. 3 is a similar section of the valve with the valve closure member in an intermediate position.

The valve 10 illustrated in FIGS. 1 to 3 is for an anaesthetic rebreathing system and provides for the selection of either a Mapleson A or Mapleson D system. It has an injection moulded plastics body 12 which is formed with:
- a fresh gas inlet 18;
- a fresh gas outlet 22;
- an expired gas inlet/outlet port 26;
- waste gas outlet 30; and
- a reservoir bag inlet/outlet port 34.

The valve body 12 has a number of conduits moulded integrally therein. The conduits include:
- a fresh gas conduit 36, which is in communication with the fresh gas inlet 18 and the fresh gas outlet 22;
- an expired gas conduit 38, which is in communication with the expired gas inlet/outlet port 26 and the waste gas outlet 30; and
- a reservoir bag conduit 40, which is in communication with the reservoir bag inlet/outlet port 34.

The conduits all have large cross sectional areas and this allows gas to be conducted with minimal resistance to flow.

All three conduits 36, 38 and 40 converge at a node 42 constituted by a slideway within which a complemental valve closure member 44 is slidable. The valve closure member 44 comprises two right circular cylindrical plugs 46 which are joined together by a central neck region 48 of reduced diameter. The right circular cylindrical plugs 46 are hollow moulded to mitigate jamming, the walls of the plugs being flexible so that the valve closure member 44 may be easily released by simple manipulation thereof if it becomes jammed in the node 42.

The valve 10 also includes an adjustable screw valve 49 which can be used to vary the expired gas back pressure in the expired gas conduit 38. The body 50 of the adjustable screw valve 49 tapers frusto-conically and ends in an elongate spindle 60 which is rotatably housed in a complemental hole in the valve body 12, to facilitate axial stability of the screw valve 49. The body of the adjustable screw valve 49 mates with a complemental valve seat 62 and is prevented from being removed from the spindle hole in the valve body 12 by a retaining ring 64 located at the end of the elongate spindle 60. In the closed position, the body of the screw valve 49 occludes the waste gas outlet 30 completely. In other positions of the screw valve 49 the outlet 30 is open to varying degrees.

The valve closure member 44 is slidable between a first and a second position, but should the operator not slide the valve closure member 44 fully either way, it will, in any intermediate position, interconnect all three conduits 36, 38 and 40. The neck region 48 of the valve closure member 44 has a diameter small enough to allow all three conduits 36, 38 and 40 to be in communication when the valve closure member 44 is in an intermediate position, as shown in FIG. 3. The benefits of the interconnection of the three conduits 36, 38 and 40 will be set out below.

FIG. 1 shows the valve closure member 44 in the first position. This corresponds to a Mapleson A system configuration—spontaneous breathing in the patient—with the fresh gas inlet 18 and the fresh gas outlet 22 in communication with the reservoir bag inlet/outlet port 34. A constant stream of fresh gas enters the valve 10 via the fresh gas inlet 18, flows down the fresh gas conduit 36, through the reservoir bag inlet/outlet port 34 and into the reservoir bag (not shown). From there fresh gas flows back up the fresh gas conduit 36 and out of the fresh gas outlet 22 which leads to the inspiratory limb (not shown) of the anaesthetic system. Expired gas flows from the expiratory limb (not shown) of the anaesthetic system through the expired gas inlet/outlet port 26, into the expired gas conduit 38 and out of the waste gas outlet 30. The screw valve 49 is withdrawn and does not occlude the waste gas outlet 30. A gas scavenging system (not shown) may be attached to the waste gas outlet 30 for the purpose of removing expired gas from the theatre.

FIG. 2 shows the valve closure member 44 in the second position. This corresponds to a Mapleson D system configuration—controlled breathing in the patient—with the expired gas inlet/outlet port 26 and the waste gas outlet 30 in communication with the reservoir bag inlet/outlet port 34. This allows constant stream of fresh gas to enter the valve 10 via the fresh gas inlet 18 but prevents it from flowing through the reservoir bag inlet/outlet port 34 into the reservoir bag. The fresh gas flows into the fresh gas conduit 36 and out of the fresh gas outlet 22 which leads to the inspiratory limb of the anaesthetic system. Expired gas flows from the expiratory limb of the anaesthetic system, through the expired gas inlet/outlet port 26 and into the expired gas conduit 38. Some of this gas flows out through the waste gas outlet 30, which may be partly occluded by the screw valve 49. The remainder of the expired gas flows down the expired gas conduit 38 through the reservoir bag inlet/outlet port 34 and into the reservoir bag.

FIG. 3 shows the valve closure member 44 in a position intermediate the first and second positions thereof, a situation which could occur during switching between the first and second positions. It could also occur accidentally, should the operator of the system not push the closure member fully home in either the first or the second positions. In the intermediate position, the fresh gas inlet 18, the fresh gas outlet 22, the expired gas inlet/outlet port 26 and the waste gas outlet 30 are all in communication with the reservoir bag inlet/outlet port 34. This configuration should, of necessity, be a temporary one. It prevents the reservoir bag inlet/outlet port 34 from ever being isolated from the fresh gas inlet 20, the fresh gas outlet 22, the waste gas outlet 18 and the expired gas inlet/outlet port 26 simultaneously and allows any pressure increase to be absorbed by the compliant reservoir bag instead of being transmitted to the patient through the inspiratory or expiratory limbs.

The component parts of the valve 10 are shaped in such a way as to facilitate correct assembly of the valve. The valve 10, after normal attachment to an anaesthetic gas supply machine is oriented in such a way that the inspiratory and expiratory limbs point towards the patient with the reservoir bag dependent. The expiratory limb connector is located at the top of the valve and is well positioned to receive an external pressure relief valve if the user prefers to fit such a relief valve. The expiratory limb connector is also well placed to receive a scavenger system to override the integral pressure relief valve which would, in this situation be closed to occlude the waste gas outlet fully.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A valve for an anaesthetic rebreathing system including a valve body and a valve closure member situated within the valve body, the valve body including a fresh gas inlet, a fresh gas outlet, a fresh gas conduit in communication with the fresh gas inlet and the fresh gas outlet, an expired gas inlet/outlet port, a waste gas outlet, an expired gas conduit in communication with the expired gas inlet/outlet port and the waste gas outlet, a reservoir bag inlet/outlet port and a reservoir bag conduit in communication with the reservoir bag inlet/outlet port, the conduits converging at a node within which the valve closure member is operable to move between a first, intermediate and second position, the intermediate position being between the first and second positions, the valve closure member isolating the expired gas inlet/outlet port and the waste gas outlet from the reservoir bag inlet/outlet port in the first position thereof and isolating the fresh gas inlet and the fresh gas outlet from the reservoir bag inlet/outlet port in a second position thereof and when the valve closure member is in the intermediate position thereof, the fresh gas inlet, the fresh gas outlet, the expired gas inlet/outlet port and the waste gas port are all in communication with the reservoir bag inlet/outlet port.

2. The valve according to claim 1, which includes a back pressure control for controlling back pressure in the expired gas conduit, the back pressure control being adjustable between a first setting in which expired gas freely flows out of the waste gas outlet and at least one other setting in which the waste gas outlet is at least partly occluded.

3. The valve according to claim 2, wherein in a first setting of the back pressure control the back pressure in the expired gas conduit is maintained at a relatively low level and in at least one other setting the back pressure in the expired gas conduit is maintained at a higher level.

4. The valve according to claim 2 or claim 3, wherein the back pressure control is an adjustable screw valve.

5. The valve according to any one of claims 1 to 3, wherein the valve body is an injection moulded plastics body with the fresh gas conduit, the expired gas conduit and the reservoir bag conduit all integrally moulded therein.

6. The valve according to any one of claims 1 to 3, wherein the valve closure member comprises a pair of cylindrical plugs which are joined to each other by a central neck region of reduced cross-section, the pair of cylindrical plugs acting as two independent valve closure members, each at its own seat, which are movable within the node.

7. The valve according to claim 6, wherein the node is a slideway, complemental to the valve closure member, into which the fresh gas conduit, the expired gas conduit and the reservoir bag conduit all open, the neck region of the valve closure member being dimensioned to interconnect all the conduits opening into the node when the valve closure member is in the intermediate position, the valve closure member being slidable between the first, intermediate and second positions.

8. The valve according to any one of claims 1 to 3, wherein the waste gas outlet is adapted for connection to a waste gas scavenging system.

9. The valve according to claim 4, wherein the adjustable screw valve has a frusto-conical valve member which mates with a complemental valve seat.

* * * * *